United States Patent
Bornstein et al.

(10) Patent No.: US 6,572,842 B1
(45) Date of Patent: *Jun. 3, 2003

(54) PREPARATION FOR DENTAL TREATMENT

(75) Inventors: Rolf Bornstein, Stockholm (SE);
Lennart Carlsson, Goteburg (SE);
Stefan Dahlin, Hovas (SE)

(73) Assignee: Mediteam Dental, AB, Savedalen (SE)

( * ) Notice: Subject to any disclaimer, the term of this patent is extended or adjusted under 35 U.S.C. 154(b) by 0 days.

This patent is subject to a terminal disclaimer.

(21) Appl. No.: 09/889,483

(22) PCT Filed: Dec. 22, 1999

(86) PCT No.: PCT/SE99/02457

§ 371 (c)(1),
(2), (4) Date: Oct. 17, 2001

(87) PCT Pub. No.: WO00/42975

PCT Pub. Date: Jul. 27, 2000

(30) Foreign Application Priority Data

Jan. 19, 1999 (SE) ................................................ 9900147

(51) Int. Cl.$^7$ .......................... A61K 7/20; C11D 3/395; C01B 11/66
(52) U.S. Cl. .......................... 424/53; 510/369; 510/379; 510/383; 510/359; 252/186.25; 252/187.25; 252/187.26
(58) Field of Search ........................................... 424/53

(56) References Cited

U.S. PATENT DOCUMENTS

| | | | | |
|---|---|---|---|---|
| 3,684,722 A | * | 8/1972 | Hynam et al. ................. 252/98 |
| 3,903,252 A | * | 9/1975 | Stearns et al. ................ 424/49 |
| 3,956,158 A | * | 5/1976 | Donaldson ................... 252/102 |
| 4,271,030 A | * | 6/1981 | Brierley et al. ................ 252/88 |
| 4,585,570 A | * | 4/1986 | Nelson ........................ 252/102 |
| 5,026,523 A | * | 6/1991 | Taya ............................ 422/16 |
| 5,688,756 A | * | 11/1997 | Garabedian et al. ......... 510/369 |
| 5,697,985 A | * | 12/1997 | Good et al. ..................... 8/528 |
| 5,827,810 A | * | 10/1998 | Brodbeck et al. ........... 510/369 |
| 5,851,421 A | * | 12/1998 | Choy et al. ............. 252/187.26 |
| 5,997,764 A | * | 12/1999 | Ambuter et al. ....... 252/186.25 |
| 6,017,515 A | * | 1/2000 | van den Bosch ............. 424/53 |
| 6,083,422 A | * | 7/2000 | Ambuter et al. ....... 252/187.26 |
| 6,099,310 A | * | 8/2000 | Bornstein et al. ........... 433/141 |
| 6,100,228 A | * | 8/2000 | Argo et al. ................. 510/379 |

FOREIGN PATENT DOCUMENTS

| | | | |
|---|---|---|---|
| EP | 398893 | * | 10/1993 |
| EP | 0 398 893 B1 | | 10/1993 |
| SE | 460258 | * | 9/1989 |
| WO | 97/19597 | * | 6/1997 |
| WO | 98/20838 | * | 5/1998 |
| WO | 99/34765 | * | 7/1999 |
| WO | 00/42974 | * | 7/2000 |

* cited by examiner

*Primary Examiner*—Shep K. Rose
(74) *Attorney, Agent, or Firm*—Connolly Bove Lodge & Hutz, LLP

(57) ABSTRACT

The invention relates to a preparation for chemical-mechanical treatment of caries by means of a caries-dissolving two-component liquid. One of the components is an active, caries dissolving component and the other a component which reduces the aggressiveness of the active component to mucous membranes. The active component is a chloride compound comprising active chlorine, i.e. chlorine having a charge state of +1, Cl(+1), which chloride has a somewhat lower reactivity than sodium hypochlorite and then also a somewhat reduced dissolving effect on the carious substance.

9 Claims, No Drawings

PREPARATION FOR DENTAL TREATMENT

REFERENCE TO RELATED APPLICATION

This Application is a 371 of PCT/SE99/02457, filed Dec. 22, 1999, which claims the priority of SE 9900147-1, filed Jan. 19, 1999. The instant application further claims the priority of PCT/SE99/00005, International Publication Number WO99/34765, filed Jan. 7, 1999, which claims the priority of SE 9800025-0, filed Jan. 9, 1998, and of PCT/SE97/01887, International Application Number WO98/20838, filed Nov. 11, 1997, which in turn claims the priority of SE 9604210-6, filed Nov. 14, 1996.

The present invention relates to a preparation for chemical-mechanical treatment of caries by means of a caries-dissolving two-component liquid in the form of an active, caries dissolving component and a component which reduces the reactivity and the aggressiveness of the active component to healthy tissue.

In traditional caries treatment the attacked tooth substance is removed mechanically by means of a high-speed drill. Such a caries treatment is often a painful and unpleasant experience for the patient. Some of the patients feel so uncomfortable with the treatment that they wait far too long before they go to the dentist, which means that it is often too late to save the caries attacked teeth. Extraction of the teeth is then the only treatment method that is left.

However, there are other methods which are based on a chemical-mechanical treatment for the removal of the caries attacked tooth substance. A method of this type is described in SE 460258. According to this method a two-component liquid is mixed and then immediately applied on the caries lesion. Functioning in a biological way, the liquid makes the caries attacked substance soft without causing any damage to the tooth or the soft tissue. After 10–15 seconds the dentist can start removing the softened carious substance by scraping. The scraping procedure continues until all carious substance has been removed. Then the cavity is sealed with a suitable filling material.

According to the patent the two-component liquid consists of a sodium hypochlorite component and an amino acid component. The amino acid component consists of three amino acids with different charge states in the side chain. The object of the amino acids is to reduce the reactivity of the hypochlorite component, and then also the aggressivity, to healthy tissue and to direct the desired effect to proteins. This is achieved by a chlorination of the amino groups in the amino acids by the hypochlorite which is then consumed.

Unlike the conventional mechanical caries treatment this biological treatment method is usually not painful at all. Neither does it require any investments in expensive equipments.

According to the treatment method the mixed two-component liquid is applied in drops on the tooth so that the entire carious lesion is covered and the caries affected tissue is softened. After 10–15 seconds a mechanical removal of the softened carious substance can be started. The softened carious dentine (the tooth substance) is removed with the use of a scraping instrument. After some scraping the solution becomes turbid due to suspended carious substance and can be exhausted by suction or wiped away.

The above steps are repeated until the solution remains clear. In order to minimize any discomfort and pain for the patient any removal of the solution by means of a cold air stream or cold water flushing should be avoided. Instead, cotton pellets are used to remove the solution. When the carious substance has been completely removed the cavity is sealed with a suitable filling material.

For most carious lesions the treatment has to be repeated in several steps until the solution remains clear. Due to the repetition of the procedure a relatively large volume of the two-component liquid is required. Since the liquid has a low viscosity it is easily dispersed outside the carious lesion and there is a risk for liquid waste on the surrounding tissue. It might be difficult and/or time-consuming for the dentist to remove such a solution which has been spread or which has been unintentionally spilt outside the carious lesion.

In order to facilitate the handling of such a two-component liquid it is previously known to add a viscosity increasing substance (gel substance) and a coloring agent to the liquid, see SE 96.04210-6. The gel substance should then have such properties that the aggressive influence of the sodium hypochlorite on mucous membranes is reduced, preferably it is a carboxy methyle cellulose, and the coloring agent should have the ability to interact with the carious substance. According to a preferred embodiment the coloring agent consists of Erythrosin (E 127 B).

In addition to the fact that the gel substance and the coloring agent facilitate the application of the preparation by making it more visible and viscous, they have also other advantages in connection with the removal of carious substance. During the treatment of the carious lesion with the additional gel substance the turbidity that appears is an indication of the fact that still more carious tooth substance has to be removed. More gel substance is then applied until no more turbidity appears. This is an indication that all carious substance has been removed. The coloring agent has been introduced for indicating carious tooth substance, in the tooth itself before it has been removed, but also in the gel substance to make the turbidity more visible as the suspended particles in the solution are colored.

Even if it is previously known to use other reactivity reducing components than the above-mentioned amino acids, for instance a gel component according to Swedish patent application 98.00025-0, sodium hypochlorite has been used so far for the active component. The advantage by using sodium hypochlorite is the fact that it has a high reactivity and therefore a rapid and efficient effect on caries. The disadvantage, on the other side, is the fact that it is rapidly consumed so that it might be difficult to control the treatment procedure.

The high reactivity of sodium hypochlorite means that it breaks down almost everything in its way, which makes it toxic in biological tissue. It must be handled very carefully in order to avoid the risk of corroding effects. It must be stored cold and in darkness.

It is an object of the present invention to provide a carious-dissolving preparation which is more easy to handle and which reduces the risk of damaging or affecting biological tissue outside the carious lesion.

It has then turned out that also other chloride compounds than sodium hypochlorite which comprises active chlorine, ie chlorine with a positive charge +1, Cl(+1),—when mixed with a suitable reactivity reducing component—have a caries dissolving effect. It has not previously been expected that these types of chloride compounds should have a sufficient caries dissolving effect as the reactivity, from a general point of view, is lower than for sodium hypochlorite. However, the lower reactivity also increases the lifetime of the mixture (preparation), reduces the formation rate of chloramine so that the time for action increases. This, in turn, means that the reaction zone of the treatment is increased which makes the treatment procedure more easy and simple to control. The preparation can be used more effectively and makes the treatment as a whole as effective as the use of the more reactive sodium hypochlorite.

Such a "delayed reaction" of the preparation can be especially useful for certain types of carious lesions, such as carious lesions with mineralized zones, in which case the preparation is allowed to act on these zones for a comparatively long time compared to previous treatment procedures.

It can also be especially benefical to use the preparation in such cases in which a somewhat lower reactivity is desired for other reasons, for instance in the treatment of patients with specifically sensitive mucous membranes.

A further advantage by using this type of chlorine compounds instead of sodium hypochlorite is the fact that the component is more easily handled and the storage durability is prolonged.

According to the invention the preparation consists of a chloride compound component of active chlorine, ie chlorine having a charge state of +1, Cl(+1), which chloride has a somewhat lower reactivity than sodium hypochlorite and then also a somewhat reduced dissolving effect on the carious substance, and a reactivity reducing component which, when mixed with the chloride compound component, interacts with the chloride compound, and gives rise to compounds containing active chlorine which, while retaining a caries-dissolving quality, does not show the aggressiveness of chloride compounds towards mucous membranes.

"Active chlorine" or chlorine having a charge state of +1, Cl(+1), is too reactive to exist as a free ion. However, it exists in many combinations with other atoms, with different reactivity, such as in simple salts, usually together with oxygen. Some examples of such chloride compounds is potassium hypochlorite (KOCl), calcium hypochlorite (Ca(OCl)2) and ammonium hypochlorite (NH4OCl). However, the chlorine ion can also be bound to carbon, oxygen or nitrogen in an organic compound. Examples of such chloride compounds are substituted dichloramine (RNCl2, where R is some other chemical compound or structure, bound to nitrogen, N, for instance a carbon chain), single chloramine (NH2Cl), substituted (mono)chloramine (RNHCl) or the like. A common feature for these chloride compounds is the contents of active chlorine and a reactivity which is less than the reactivity of sodium hypochlorite.

The object of the reactivity reducing component is to reduce the aggressivity of the preparation to healthy tissue and direct the desired effect towards proteins. This object can be achieved according to the above-mentioned SE 460258 by chlorination of the amino group of the amino acids. However, the acid itself in the amino acid compounds, ie the carboxy group which per definition belongs to each amino acid, has primarily nothing to do with the desired reactivity reducing function, other than affecting the ion activity of the solution and the pH buffering, which also can be achieved by other means. It is the amino part of the amino acid which is chlorinated, and such chlorination is the same for all amines and not just for amino acids. All chloramines then have a potential caries dissolving effect. According to the invention therefore the reactivity reducing component is preferably a component comprising amines, ie compounds comprising $NH_x$, where x=1, 2 or 3, and which can be bound to one or several other chemical compounds, for instance carbon chains.

Another example of a suitable reactivity reducing component is a gel substance component known per se, for instance 2–10% carboxy methyl cellulose which concentration is sufficient for the gel substance alone to reduce the aggressive influence of the sodium hypochlorite on mucous membranes. Preferably, the gel substance component also comprises a coloring agent of 0.04% Erythrosin (E 127 B), acid red or Xantene. Such a component is described more in detail in SE 96.04210-6.

Even if the life-time of the caries-dissolving solution according to the invention is somewhat longer than the previously used preparations it is important that the solution is used immediately in order to have a good effect. In this connection the carboxy methyl cellulose has the advantage that the viscosity of the gel is dramatically reduced when the solution mixed with the chloride compound component gradually becomes inactive with respect to its caries-dissolving ability. The degradation will be clearly visible after approximately 30 minutes in room temperature as the liquid then has lost most of its viscosity. The gel substance then functions, as previously, as an indicator when the solution becomes inactive for caries dissolution.

In the following two examples of a caries dissolving two component solution according to the invention will be described more in detail, in which the reactivity reducing component has been indicated by A and the active component by B.

As illustrated in the example the active component is a chloride compound, 0.5% calcium hypochlorite (example 1) and 0.5% potassium hypochlorite (example 2), respectively.

EXAMPLE 1

A. A solution (red) in clean (de-ionized) water consisting of:

| | | |
|---|---|---|
| L-glutamine acid | $C_5O_4NH_9$ | 34 mM |
| L-leucine | $C_6O_2NH_{13}$ | 38 mM |
| L-lycine | $C_6O_2N_2H_{14}$ | 34 mM |
| Erythrosin (E 127 B) | $Na_2C_{20}O_5I_4H_6$ | 0,04% (4.5 mM) |
| Sodium chloride | NaCl | 0,1 M |
| Sodium hydroxide | NaOH | to pH = 11 |
| Carboxy methyl cellulose (CMC) 200–800 mPas 3% | | |

B. A solution (clear) in clean (de-ionized) water consisting of:

Calcium hypochlorite $Ca(OCl)_2$ 0.5% (0.1 M)

EXAMPLE 2

A. A solution (red) in clean (de-ionized) water consisting of:

| | | |
|---|---|---|
| Amino-ethane-diole | $C_2O_2NH_7$ | 34 mM |
| 1-amino-3,3-dimethylepropanol | $C_5ONH_{13}$ | 38 mM |
| 1,5-diaminopentanol | $C_5ON_2H_{14}$ | 34 mM |
| Erythrosin (E 127 B) | $Na_2C_{20}O_5T_4H_6$ | 0,04%(4.5 mM) |
| Sodium chloride | NaCl | 0,1 M |
| Sodium hydroxide | NaOH | to pH = 11 |
| Carboxy methyl cellulose (CMC) 200–800 mPas 3% | | |

B. A solution (clear) in clean (de-ionized) water consisting of:

Potassium hypochlorite KOCl 0.5% (0.1 M)

INCORPORATION BY REFERENCE

All patent documents referred to herein, including all published applications and issued patents, are hereby specifically incorporated in their entirety and for all purposes.

What is claimed is:

1. A two-component preparation for chemical-mechanical treatment of caries comprising:
   a first liquid component comprising an active chlorine compound, wherein said active chlorine compound is less reactive than sodium hypochlorite; and
   a second liquid component, wherein said second component reduces the reactivity of said active chlorine compound.

2. A preparation, according to claim 1, wherein said active component comprises potassium hypochlorite and calcium hypochlorite.

3. A preparation according to claim 2 characterised in that the active component is calcium hypochlorite.

4. A preparation according to claim 2 characterised in that the active component is potassium hypochlorite.

5. A preparation according to claim 1 characterised in that the active component comprises active chlorine bound to carbon, oxygen or nitrogen in an organic compound.

6. A preparation according to claim 1 characterised in that the reactivity reducing component comprises an amino part.

7. A preparation according to claim 1 wherein said reactivity reducing component comprises a gel.

8. A preparation, according to claim 1, wherein said active component comprises ammonium hypochlorite.

9. A preparation according to claim 1, wherein said reactivity reducing component is carboxymethylcellulose.

* * * * *